United States Patent [19]

Perrine

[11] Patent Number: 5,439,939
[45] Date of Patent: * Aug. 8, 1995

[54] PHARMACEUTICAL COMPOSITIONS AND METHODS USING ISOBUTYRAMIDE FOR TREATING BETAGLOBIN DISORDERS

[75] Inventor: Susan P. Perrine, Richmond, Calif.

[73] Assignee: Children's Hospital Medical Center of Northern California, Oakland, Calif.

[ * ] Notice: The portion of the term of this patent subsequent to Jun. 18, 2008 has been disclaimed.

[21] Appl. No.: 852,511

[22] Filed: Mar. 17, 1992

[51] Int. Cl.$^6$ ............................................. A61K 31/16
[52] U.S. Cl. ..................... 514/629; 514/815
[58] Field of Search ............... 514/629, 815, 629, 815

[56] References Cited

U.S. PATENT DOCUMENTS

| | | | |
|---|---|---|---|
| 4,482,571 | 11/1984 | Abraham | 424/317 |
| 4,822,821 | 4/1989 | Perrine | 514/557 |
| 5,025,029 | 6/1991 | Perrine | 514/381 |

FOREIGN PATENT DOCUMENTS 371789  6/1990  European Pat. Off. ..... A61K 31/19

OTHER PUBLICATIONS

Chemical Abstracts 111(13): 110867f, 1989, Lundquist et al.
*Aldrich Handbook of Organic Chemicals*, Aldrich Chemical Co., Inc., 1972, U.S.A., p. 385.
Goodman Gilman et al. (Editors), *The Pharmacological Basis of Therapeutics* (6th Ed.), New York, MacMillan, 1980, p. 15.
Perrine, S., et al., "Butyric Acid Analogues Augment γ Globin Gene Expression in Neonatal Erythroid Progenitors," *Biochem. Biophys. Res. Commun.* 148(2):694–698 (1987).
Perrine, S., et al., "Inhibition of fetal globin gene switching in vivo in human and ovine fetuses," Alan R. Liss, Inc.: *Developmental Control of Globin Gene Expression* 545–554 (1987).
Perrine, S., et al., "Butyrate infusions in the ovine fetus delay the biologic clock for globin gene switching," *Proc. Natl. Acad. Sci. USA* 85:8540–8542 (Nov. 1988).
Perrine, S., et al., "Sodium Butyrate Enhances Fetal Globin Gene Expression in Erythroid Progenitors of Patients With Hb SS and β Thalassemia," *Blood* 74(1):454–459 (Jul. 1989).
Perrine, S., et al., "Butyrate analogues modulate globin gene expression in human and ovine ertyhroid cells," Alan R. Liss, Inc.: *Hemoglobin Switching, Part B: Cellular and Molecular Mechanisms* 341–350, (1989).
Perrine, S., et al., "Stopping the Biologic Clock for Globin Gene Switching," *Sixth Cooley's Anemia Symposium: Annals of the New York Academy of Sciences*, 612:134–140 (1990).
Perrine, S., et al., "Pharmacologic prevention and Reversal of Globin Gene Switching," The Johns Hopkins University Press: *The Regulation of Hemoglobin Switching* 425:436 (1991).
Constantoulakis, P. et al., Trans. Assoc. Am. Physicians 103: 80–89 (1990).
Constantoulakis, P. et al., "Alpha–amino–n–butyric Acid Stimulates Fetal Hemoglobin in the Adult", Blood 72: 1961–1967 (1988).
Daniel, P. et al., "Pharmacokinetic Study of Butyric Acid In Vivo as Sodium and Arginine Butyrate Salts", Clin. Chem. Acta 181: 255–263 (1989).
Karlsson, S. and Nienhuis, A. W., "Developmental Regulation of Human Globin Genes", Annu. Rev. Biochem. 54: 1071–1108 (1985).
Miller, A. A. et al., Eur. J. Cancer Clin. Oncol. 23: 1283–1287 (1987).

(List continued on next page.)

Primary Examiner—Marianne M. Cintins
Assistant Examiner—M. Moezie
Attorney, Agent, or Firm—Fish & Neave; James F. Haley, Jr.; Margaret A. Pierri

[57] ABSTRACT

This invention relates to treatment of betaglobin disorders, such as sickle-cell anemia and beta-thalassemia, by administering compositions of isobutyramide.

8 Claims, 2 Drawing Sheets

OTHER PUBLICATIONS

Murata et al., J. Ferment. Technol. 66(5): 501–507 (1988).

Noguchi et al., "Levels of Fetal Hemoglobin Necessary for Treatment of Sickle Cell Disease", N. Eng. J. Med. 318: 96–99 (1988).

Olivieri, N. F. et al., "Butyrate Stimulates Gamma-Globin Synthesis in Patients with Beta-globin Gene Disorders", Blood 78: 368a (1991).

S. P. Perrine, et al., "An Orally Bioavailable Butyrate Analog Stimulates Fetal Globin Gene Expression In Vivo", *Abstract in the 17th Annual Sickle Cell Disease Conference Meharry Medical College*, p. 140a (Mar. 14, 1992).

S. P. Perrine, "Pharmacological Modulation of Fetal Globin Gene Expression in the Perinatal Period", Semin. Perinatol., 14(5): 346–350 (1990).

S. P. Perrine et al., "Butyric Acid Modulates Developmental Globin Gene Switching in Man and Sheep", Adv. Exp. Med. Biol., 271: 177–183 (1989).

Perrine, S. P. et al., "Sodium Butyrate Enhances Fetal Globin Gene Expression in Erythroid Progenitors of Patients with Hb SS and Beta-Thalassemia," Blood 74(1): 454–459 (Jul. 1989).

Perrine, S. P. et al., "Delay in the Fetal Globin Switch in Infants of Diabetic Mothers", N. Engl. J. Med. 312: 334–338 (1985).

Schechter, A. N. and Noguchi, C. T., "Inhibition of Sickle Hemoglobin Gelation by Peptides", In: Development of Therapeutic Agents for Sickle Cell Disease, eds. J. Rosa, Y. Beuzard and J. Hercules, North-Holland Publishing Company, Amsterdam-New York-Oxford (1979).

Tsuji et al., "Structural and Biological Identity of Recombinant EDF (Erythroid Differentiation Factor) with Natural EDF", Agric. Biol. Chem. 52(9): 2143–2148 (1988).

Wood, W. G., et al., "HbF Synthesis in Sickle Cell Anemia: a Comparison of Saudi Arab Cases with Those of African Origin", Br. J. Haematol. 45: 431–445 (1980).

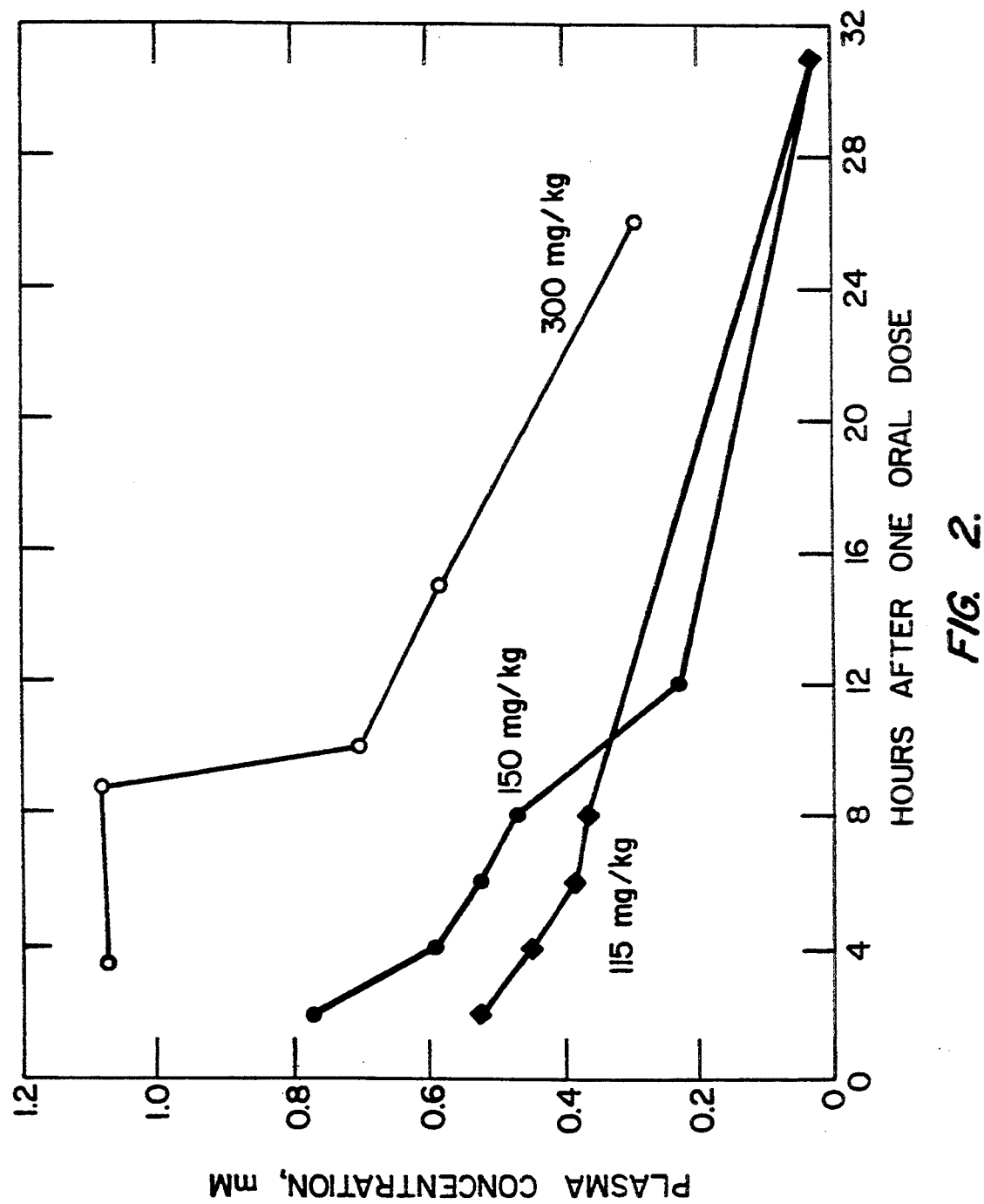

PHARMACEUTICAL COMPOSITIONS AND METHODS USING ISOBUTYRAMIDE FOR TREATING BETAGLOBIN DISORDERS

The U.S. Government has a paid-up license in this invention and the right in limited circumstances to require the patent owner to license others on reasonable terms as provided for by the terms of grant no. 37118 awarded by the Heart, Lung, and Blood Institute, Department of Health and Human Services.

BACKGROUND OF THE INVENTION

Betaglobin is a polypeptide subunit of hemoglobin A, the principal hemoglobin in adult humans. Hemoglobin A is the principal oxygen carrier in blood. Hemoglobin A is made up of four subunits, two alphaglobin chains and two betaglobin chains. Several diseases are characterized by the production of abnormal betaglobin and impaired hemoglobin S, as in sickle-cell anemia, or from the production of no or deficient amounts of betaglobin and hemoglobin A, as in beta-thalassemia. These diseases have long been recognized to arise from genetic defects, such as a single mutation in the betaglobin gene in sickle-cell anemia.

There is no pharmaceutical composition or method in use for the effective treatment of betaglobin disorders.

SUMMARY OF THE INVENTION

This invention is directed to pharmaceutical compositions and methods employing isobutyramide for treating disorders arising from betaglobin deficiencies. This invention relates to use of isobutyramide to treat these disorders by stimulating production of fetal hemoglobin, hemoglobin F.

BRIEF DESCRIPTION OF THE DRAWINGS

FIG. 2 shows the plasma concentrations of isobutyramide at various times after administration of a single oral dose to human subjects (expressed in mM).

DESCRIPTION OF THE INVENTION

Figure 1:
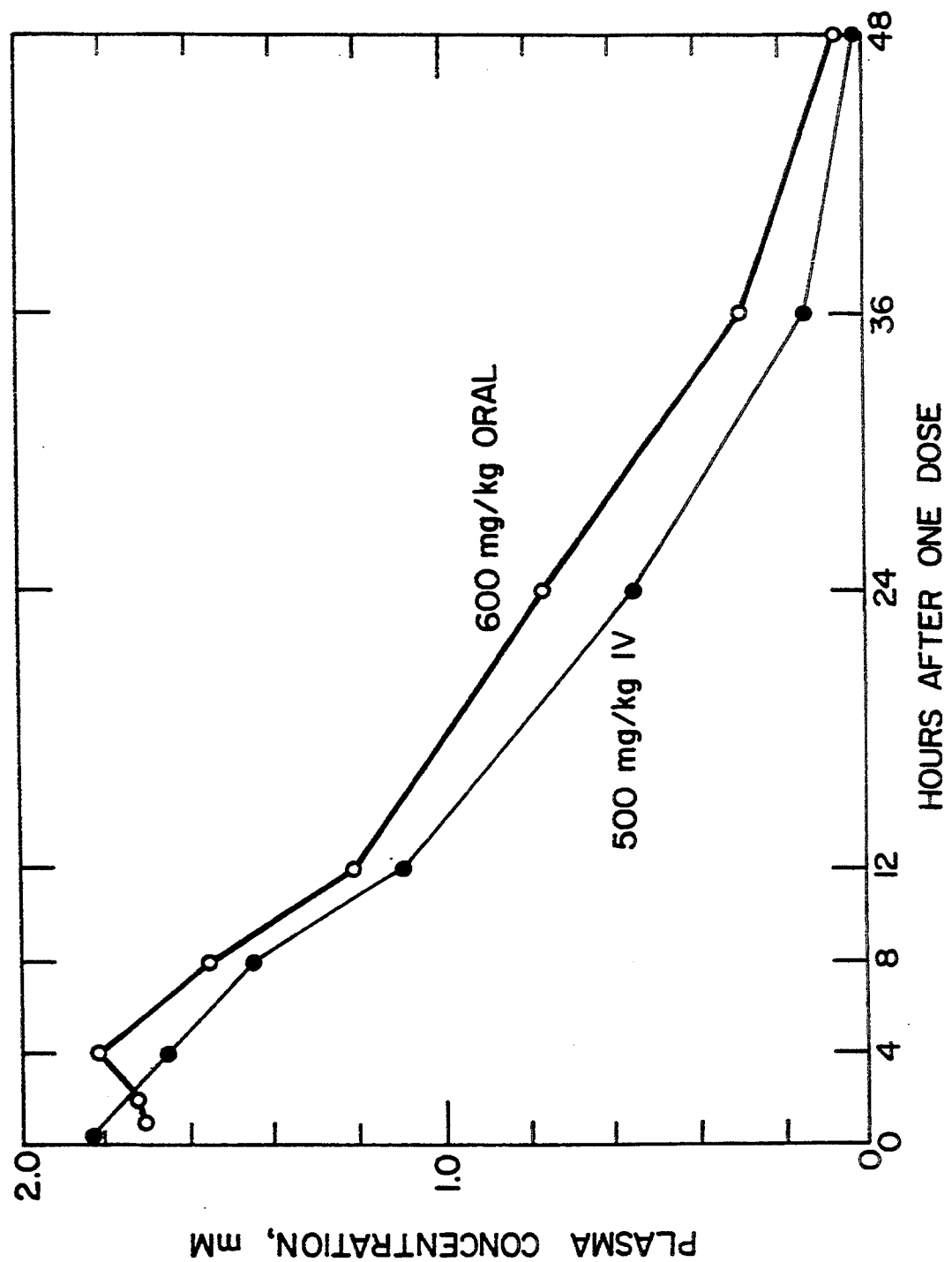
FIG. 1 shows the plasma concentrations of isobutyramide at various times after administration of a single oral dose to baboons (measured by gas liquid chromatography and expressed in mM).

The invention provides pharmaceutical compositions containing isobutyramide and methods for treating betaglobin disorders by administering isobutyramide.

Isobutyramide is a chemical having the formula $(CH_3)_2CHCONH_2$. Isobutyramide may be produced by routine synthesis procedures and is available from chemical suppliers, such as Aldrich Chemical Co.

The pharmaceutical compositions of this invention contain isobutyramide. These compositions are useful in treatment of disorders involving the failure to produce normal betaglobin entirely or in sufficient amounts. The production of abnormal betaglobin or the production of betaglobin in insufficient amounts leads to the production of abnormal hemoglobin, such as hemoglobin S, or deficient amounts of hemoglobin A. These disorders are generally referred to as beta-hemoglobinopathies and beta-thalassemias. They are referred to here simply as betaglobin disorders. The most common disorders of this type are sickle-cell anemia and beta-thalassemia. Examples of other betaglobin disorders are hemoglobin C, hemoglobin E, hemoglobin Lepore, hemoglobin SC, hemoglobin S-beta 0 or + thalassemia, hemoglobin E-beta-thalassemia, delta beta-thalassemia, and other combinations of these disorders.

The compositions and methods of this invention are useful for treatment of the betaglobin disorders in mammals, including humans. These compositions and methods stimulate the production of fetal hemoglobin, also referred to as hemoglobin F, to a level that achieves therapeutic treatment of these disorders. Therapeutic treatment of these disorders may involve administration to patients prophylactically, that is to prevent, retard, or reduce the severity of future occurrence of the disease or its clinical manifestations. The ability of isobutyramide to stimulate production of fetal hemoglobin permits a new practical therapy of these conditions.

The compositions of the invention contain a therapeutically effective amount of isobutyramide with a pharmaceutically acceptable carrier. A pharmaceutically acceptable carrier may be any compatible, non-toxic substance suitable to deliver the isobutyramide to the patient. The compositions may contain other pharmaceutically acceptable substances as required to approximate physiological conditions such as pH adjusting and buffering agents, dispersing agents, toxicity adjusting agents, flavoring agents and the like. The concentration of isobutyramide in these formulations may vary and will be selected primarily based on the particular dosage and mode of administration selected. Methods for preparing administrable compositions are well known to those skilled in the art. The pharmaceutical compositions of isobutyramide are useful for oral or parenteral administration. The compositions may be formulated in a variety of dosage forms, such as tablets, capsules, oral solutions or suspensions, sterile parenteral solutions or suspensions, transcutaneous patches, slow-release implants, and indwelling implant devices.

Preferably, the pharmaceutical compositions are administered orally. For oral administration, solid or fluid dosage forms can be prepared. For preparing solid compositions such as tablets, the isobutyramide is mixed with conventional ingredients, such as talc, magnesium stearate, and functionally similar materials, as pharmaceutical carriers. Capsules are prepared by mixing the isobutyramide with an inert pharmaceutical diluent and filling the mixture into a hard gelatin capsule. Soft gelatin capsules are prepared by machine encapsulation of a slurry of the isobutyramide with an acceptable vegetable oil, light liquid petrolatum or other inert oil. Fluid unit dosage forms for oral administration such as syrups and suspensions can be prepared. The isobutyramide can be dissolved in an aqueous vehicle together with sugar, sweetening and flavoring agents and preservatives to form a syrup. Suspensions can be prepared with an aqueous vehicle and a dispersing agent such as acacia, tragacanth, methylcellullose and the like.

This invention also provides compositions for parenteral administration, i.e. subcutaneous, intramuscular, intravenous, or transcutaneous administration. For parenteral administration, fluid dosage forms are prepared utilizing the isobutyramide and a sterile carrier, water being preferred. The isobutyramide, depending on the carrier and concentration used, may be either suspended or dissolved in the carrier. In preparing solutions, the isobutyramide can be dissolved in water and sterilized before filling into a suitable vial or ampule. Adjuvants such as a local anesthetic, preservative and buffering agents can be dissolved in the carrier. The compositions can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compositions are suspended in the carrier instead of being dissolved. A surfactant or wetting agent is included in the compositions to facilitate uniform distribution of the isobutyramide.

The compositions containing isobutyramide may be administered for the therapeutic treatment of betaglobin disorders, including prophylactic treatment. In treatment of patients diagnosed with a betaglobin disorder, compositions are administered to a patient in an amount sufficient to produce fetal hemoglobin at levels that reduce the severity of the betaglobin disorder or its clinical manifestations. In prophylactic treatment, the compositions may be administered to a patient who may be at risk of having a betaglobin disorder, but has not been diagnosed as having such a disorder. In prophylactic therapy, compositions are administered to such a patient in an amount sufficient to produce fetal hemoglobin at levels that prevent, retard or reduce the severity of the betaglobin disorder or its clinical manifestations. An amount adequate to accomplish any of these effects is referred to as a "therapeutically effective" amount. Unit dosages effective for this use will depend upon the severity of the disorder and the general state of the patient's health, but generally will range from about 5 to about 500 mg of isobutyramide per kilogram of body weight, with dosages of from 10 to 250 mg per kilogram being commonly preferred, and dosages of about 15 to 200 mg per kilogram more preferred. The compositions are administered in multiple unit dosages over a period of time with a frequency and duration sufficient to yield a "therapeutically effective" amount, i.e., an amount sufficient to produce fetal hemoglobin at levels that reduce the severity of the betaglobin disorder or its manifestations. The frequency and duration of administration will also depend upon the severity of the disorder and the general state of the patient's health, but generally will range from about 1 dose per week to about 7 doses per week, with doses of about 3 to 5 doses per week being commonly preferred. The frequency of administration may vary during a course of therapy, but generally a higher frequency is used at the beginning of treatment. The duration of treatment will typically be for the lifetime of the patient. Isobutyramide is substantially non-toxic, when administered in therapeutically effective amounts. Isobutyramide has an acute intravenous LD 50 of about 3 g per kilogram and is not mutagenic by standard assays. In life-threatening cases, it may be desirable for the treating physician to administer these compositions in substantial excesses of these amounts. In any event, the pharmaceutical compositions should provide a quantity of the isobutyramide sufficient to effectively treat the patient.

The administration of the compositions may begin at any time. The administration may begin and continue prior to birth by administration to the mother or may begin and continue after birth. The administration may also begin during the period after birth when natural production of significant amounts of gammaglobin and fetal hemoglobin takes place and continue after the patient has reached the age when natural production of gammaglobin and fetal hemoglobin has substantially ceased. In addition, the administration may commence after the so-called developmental "switch" from production of gammaglobin to betaglobin has been substantially completed and natural production of gammaglobin and fetal hemoglobin has substantially ceased. The administration may commence during childhood or adulthood, and continue thereafter. Accordingly, the administration may begin at any age and continue throughout any ages, including beginning treatment during and after childhood.

The compositions and methods of this invention are also useful for research using mammals without or with a betaglobin disorder, including sheep, monkeys, other non-human primates, and transgenic mice. These compositions and methods may be used to stimulate the production of fetal hemoglobin in such mammals to obtain useful information about therapeutic treatment of these disorders.

A person skilled in the art may practice the invention based on this preceding description. The following examples are provided illustrate the invention. They are not intended to limit the scope of the invention.

EXAMPLE 1

Isobutyramide Oral Formulation

A typical pharmaceutical composition useful for oral administration of isobutyramide contains 0.7 ml sterile water, 0.3 ml sucrose syrup, and 100 mg of isobutyramide.

EXAMPLE 2

Isobutyramide Parenteral Formulation

A typical pharmaceutical composition for intramuscular injection contains 1 ml sterile water, and 150 mg of isobutyramide. A typical composition for intravenous infusion contains 1 ml of sterile water and 150 mg of isobutyramide.

EXAMPLE 3

The Effect of Isobutyramide On Stimulating Fetal Hemoglobin In Vivo

Adult, male baboons (Papio anubis) were used as experimental animals. Three baboons were rendered anemic by daily phlebotomy for at least about 30 days, and maintained at hematocrit values of about 22% by daily phlebotomy. Each anemic baboon was treated with isobutyramide. One baboon (no. 767) received isobutyramide by oral formulation of 150 mg isobutyramide per ml of distilled sterile water administered through a naso-gastric tube three times per week for three weeks. This baboon received isobutyramide at a dosage of 600 mg per kg of body weight. Another baboon (no. 224) received isobutyramide by parenteral formulation of 150 mg isobutyramide per ml of distilled sterile water administered by intravenous infusion over a 30 minute period one time per day for three weeks. This baboon received isobutyramide at a dosage of 500 mg per kg of body weight. Another baboon (no. 207) received isobutyramide by parenteral formulation of 150 mg isobutyramide per ml of distilled sterile water administered by intravenous infusion over a 30 minute period one time per day for three days. This baboon received isobutyramide at a dosage of 500 mg per kg of body weight. The experiment was terminated with this baboon after three days due to an infection. Blood samples were taken throughout the course of treatment. Samples were assayed to determine the percentage of gammaglobin to total gamma-globin and betaglobin (Table 1) and the percentage of total reticulocytes containing gammaglobin, sometimes called "F-retics"

(Table 2). The assay to measure the percentage of gammaglobin to total gamma-globin and betaglobin was by the method described in Perrine, S. P., et al., Delay In The Fetal Globin Switch In Infants Of Diabetic Mothers, New Eng. J. Med. vol.312, pp.334–338 (1985). The assay to measure the percentage of total reticulocytes containing gammaglobin was performed by the method described in Rogers, G., et al., Hematologic Response of Patients with Sickle Cell Disease To Treatment with Hydroxyurea, New Eng. J. Med., vol.322, pp.1037–1045 (1990). Table 1 shows the highest percentage of gammaglobin to total gamma-globin and betaglobin achieved during treatment.

TABLE 1

Effect of Isobutyramide on Percentage of Gammaglobin to Total Gamma Plus Betaglobin

| Experimental Subject | Pre-treatment | Treatment |
| --- | --- | --- |
| 207 | 0 | 9 |
| 224 | 2 | 11 |
| 767 | 3 | 12 |

TABLE 2

Effect of Isobutyramide on Percentage of F-Retics to Total Reticulocytes

| Experimental Subject | Pre-treatment | Treatment |
| --- | --- | --- |
| 207 | 3 | 15 |
| 224 | 16 | 27 |
| 767 | 13 | 17 |

These treatments with isobutyramide significantly stimulated the production of fetal hemoglobin as shown by the increased percentage of gammaglobin to total gamma plus betaglobin (Table 1) and the increased percentage of total reticulocytes containing gammaglobin (Table 2). The stimulation of gammaglobin production by 4–8% has been shown to produce 20–30% hemoglobin F in the blood, a level sufficient to reduce the severity of the clinical manifestations of sickle-cell anemia. Wood, W. G., et al., Haemoglobin F Synthesis in Sickle Cell Anemia: A Comparison of Saudi Arab Cases with those of African Origin, Brit. J. Hematology, vol. 45, pp. 431–445 (1980). This experiment shows that the administration of isobutyramide stimulates production of fetal hemoglobin to levels sufficient to reduce the severity of the clinical manifestations of betaglobin disorders. This experiment shows that such administration of isobutyramide is effective even when administration begins after the so-called developmental "switch" from production of gammaglobin to betaglobin has been substantially completed and natural production of gammaglobin and fetal hemoglobin has substantially ceased. This experiment shows that such administration of isobutyramide is effective in adults.

EXAMPLE 4

The Effect Of Isobutyramide On Stimulating Fetal Hemoglobin In Vitro

Cultures of erythroid progenitors from peripheral blood of patients having a betaglobin disorder and normal subjects were cultured for about 14 days in presence of 0.2 millimoles per liter ("mM") isobutyramide and the percentages of gammaglobin to total gamma plus betaglobin were assayed substantially according to the methods described in Perrine, S. P. et al., Sodium Butyrate Enhances Fetal Globin Gene Expression in Erythroid Progenitors of Patients With Hb SS and Beta Thalassemia, Blood, vol.74, pp.454–459 (1989). The results are shown below in Table 3. The patients with sickle-cell anemia are identified as "SS" and with beta-thalassemia as "beta-thal." Ages are specified in years.

TABLE 3

Effect of Isobutyramide In Vitro on Percentage of Gammaglobin to Total Gamma Plus Betaglobin

| Patient Disorder | Age | Pre-treatment | Treatment |
| --- | --- | --- | --- |
| normal | newborn | 5 | 45 |
| SS | 2 | 17 | 96 |
| normal | newborn | 20 | 26 |
| SS | 10–11 | 22 | 40 |
| beta-thal | newborn | 40 | 50 |
| SS | 4 | 42 | 55 |
| normal | newborn | 69 | 72 |
| beta-thal | 28 | 70 | 64 |
| SS | 3 | 70 | 78 |
| beta-thal | 22 | 65 | 98 |

These treatments with isobutyramide significantly stimulated the production of fetal hemoglobin in culture as shown by the increased percentage of gammaglobin to total gamma-globin and betaglobin (Table 3). This experiment confirms that the administration of isobutyramide stimulates production of fetal hemoglobin to levels sufficient to reduce the severity of the clinical manifestations of betaglobin disorders. This experiment also shows that such administration of isobutyramide is effective even when administration begins after the so-called "switch" from production of gammaglobin to betaglobin has been substantially completed and natural production of gammaglobin and fetal hemoglobin has substantially ceased. This experiment shows that such administration of isobutyramide is effective in children and adults.

EXAMPLE 5

Plasma Levels Of Isobutyramide After Administration

Isobutyramide was administered orally to the baboon (no.767) and parenterally to another baboon (no.224) as described in Example 3. The plasma concentrations of the isobutyramide at various times after a single oral dose to those baboons are shown in FIG. 1 (measured by gas liquid chromatography and expressed in millimoles per liter ("mM")). Isobutyramide was administered orally to two human subjects. One human received a single dosage of isobutyramide orally in a formulation of 150 mg isobutyramide per ml of distilled sterile water, pH about 4.5, and at a dosage of 300 mg per kg of body weight. That human subject received separately a single dosage of isobutyramide orally in a formulation of 100 mg isobutyramide per ml of distilled sterile water, with a sucrose syrup for flavoring, and at a dosage of 150 mg per kg of body weight. Another human received a single dosage of isobutyramide orally in a formulation of 100 mg isobutyramide per ml of distilled sterile water, with a sucrose syrup for flavoring, and at a dosage of 115 mg per kg of body weight. The plasma concentrations (in mM) of the isobutyramide at various times after a single oral dose to those human subjects are shown in FIG. 2. These experiments show that isobutyramide may be administered orally and parenterally to obtain plasma levels sufficient to yield therapeutic effects and with a half-life of isobutyramide sufficient for practical administration. The half-life of isobutyramide in plasma was about 7.6 to 10.5 hours.

While I have described certain embodiments of the invention, it is apparent that the compositions and methods can be altered to provide other embodiments which utilize the compositions and methods of the invention. The scope of the invention is defined by the following claims rather than by the embodiments presented by way of example.

What is claimed is:

1. A method for treatment of betaglobin disorders, comprising administering to a mammal having a betaglobin disease a therapeutically effective amount of isobutyramide.

2. The method of claim 1 in which the isobutyramide is administered orally.

3. The method of claim 1 in which the isobutyramide is initially administered after the natural production of gammaglobin and fetal hemoglobin has substantially ceased.

4. The method of claim 1 in which the mammal is human.

5. The method of claim 4 in which the isobutyramide is administered orally.

6. The method of claim 4 in which the isobutyramide is initially administered after the natural production of gammaglobin and fetal hemoglobin has substantially ceased.

7. The method of claim 1 in which the isobutyramide is administered in an amount sufficient to provide from about 5 to about 500 mg per kg of body weight.

8. The method of claim 7 in which the isobutyramide is administered in an amount sufficient to provide from about 10 to about 250 mg per kg of body weight.

* * * * *

UNITED STATES PATENT AND TRADEMARK OFFICE
CERTIFICATE OF CORRECTION

PATENT NO. : 5,439,939
DATED : August 8, 1995
INVENTOR(S) : Susan P. Perrine

It is certified that error appears in the above-indentified patent and that said Letters Patent is hereby corrected as shown below:

Column 7, line 12, delete "disease" and substitute therefor -- disorder --.

Signed and Sealed this

Thirty-first Day of August, 1999

Attest:

Q. TODD DICKINSON

*Attesting Officer*     *Acting Commissioner of Patents and Trademarks*